United States Patent [19]

Hata et al.

[11] 4,263,203

[45] Apr. 21, 1981

[54] FLAME RETARDANTS FOR POLYAMIDES

[75] Inventors: Yuzo Hata, Hirakata; Katsumi Kuratani, Tawaramachi, both of Japan

[73] Assignee: Unitika Limited, Amagasaki, Japan

[21] Appl. No.: 30,767

[22] Filed: Apr. 17, 1979

[30] Foreign Application Priority Data

May 9, 1978 [JP] Japan .................................. 53-55312
May 9, 1978 [JP] Japan .................................. 53-55313

[51] Int. Cl.$^3$ .................. C07C 143/38; C07C 143/44; C07C 143/58; C08K 5/42
[52] U.S. Cl. .................. 260/45.85 H; 260/45.8 NT; 260/45.9 AM; 260/45.9 E; 260/45.9 KA; 260/45.9 R; 260/45.95 C; 260/501.12
[58] Field of Search ............ 260/45.7 SF, 45.9 K, 260/501.14, 45.8 NT, 45.9 AM, 501.12; 544/197, 199

[56] References Cited

U.S. PATENT DOCUMENTS

| | | | |
|---|---|---|---|
| 2,832,743 | 4/1958 | Libby et al. ..................... 260/501.14 |
| 3,113,120 | 12/1963 | Papero, Jr. et al. ........... 260/45.7 SF |
| 3,660,344 | 5/1972 | Michael et al. ................ 260/45.8 NT |
| 3,718,658 | 2/1973 | Summers ....................... 260/45.9 AM |
| 3,955,987 | 5/1976 | Schaar et al. ................ 260/DIG. 24 |

OTHER PUBLICATIONS

Dictionary of Organic Compounds, 1965, vol. 1, pp. 243 and 328, vol. 2, p. 1006, vol. 4, pp. 2661 and 2662.
Rehnelt, Chem. Abs., 1954, 4558i.
Scholles et al., Chem. Abs., 1971, 7576z.

*Primary Examiner*—Hosea E. Taylor
*Assistant Examiner*—R. A. White
*Attorney, Agent, or Firm*—Oblon, Fisher, Spivak, McClelland & Maier

[57] ABSTRACT

A flame retardant for imparting excellent flame retardancy to polyamides used as engineering plastics, is a reaction product obtained by reacting a benzenesulfonic acid type compound having the formula

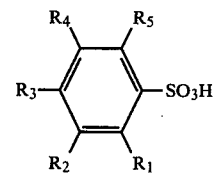

wherein $R_1$, $R_2$, $R_3$, $R_4$ and $R_5$ respectively represent H, $SO_3H$, $NH_2$, COOH, OH, CN or $NO_2$, with dicyandiamide or melamine.

16 Claims, No Drawings

FLAME RETARDANTS FOR POLYAMIDES

BACKGROUND OF THE INVENTION

1. Field of the Invention

The present invention relates to flame retardants for polyamides. More particularly, it relates to flame retardants which do not cause damage for physical properties of polyamides nor blooming on a surface of a flame retardant molded product and flame retardant polyamide compositions having flame retardancy.

2. Description of Prior Arts

Highly flame retardancy of polyamide resins have been required depending upon developments of polyamide resins for usages in electric and electronic fields and construction fields, though the polyamide itself has self-extinguishing characteristic.

Typical flame retardants for imparting highly flame retardancy to polyamide resins include halide compounds, phosphorus compounds, metal hydroxides and metal oxides. Among them, the halide compounds and antimony trioxide have been usually used as typical flame retardants.

However, it is necessary to incorporate 20 to 50% by weight of the conventional flame retardants to the polyamide resin. As the result, the physical properties of the polyamide itself are damaged and the moldability of the composition is inferior and the incorporation of the conventional flame retardant is not economical.

The organic halides themselves do not have safety or generate toxic gases in their decompositions thereof. Thus, an environmental pollution may be caused, if a large amount of said organic halide is incorporated.

Recently, nitrogen type compounds have been studied as flame retardants for polyamides. Melamine and melamine derivatives, cyanuric acid, isocyanuric acid and derivatives thereof are typical flame retardants as described in the prior arts:

U.S. Pat. No. 3,660,344 and U.S. Pat. No. 3,663,495 disclose uses of melamine and derivatives thereof, U.S. Pat. No. 3,980,616 and British Pat. No. 1,484,151 disclose uses of cyanuric acid and isocyanuric acid and U.S. Pat. No. 4,001,177 discloses use of combination of melamine or a derivative thereof and cyanuric acid or isocyanuric acid.

Flame retardancy can be given by an addition of a small amount of each of these conventional flame retardants. However, they cause blooming on a surface of a molded product whereby white powder is formed on the surface to deteriorate appearance. Sometimes, a metal contacted with the surface is corroded or a desired hue can not be given disadvantageously.

SUMMARY OF THE INVENTION

It is an object of the present invention to provide a flame retardant which has excellent flame retardancy for polyamides and does not cause blooming.

It is another object of the present invention to provide a flame retardant which does not cause toxic gas to prevent an environmental pollution.

These objects of the present invention have been attained by providing flame retardant for imparting excellent flame retardancy to polyamides which is a reaction product obtained by reacting a benzene-sulfonic acid type compound having the formula

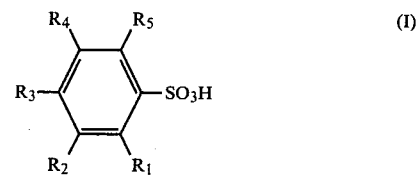

wherein $R_1$, $R_2$, $R_3$, $R_4$ and $R_5$ respectively represent H, $SO_3H$, $NH_2$, COOH, OH, CN or $NO_2$, with dicyandiamide or melamine.

DETAILED DESCRIPTION OF THE PREFERRED EMBODIMENTS

The flame retardant for polyamides is a reaction product obtained by reacting the benzenesulfonic acid type compound having the formula (I)

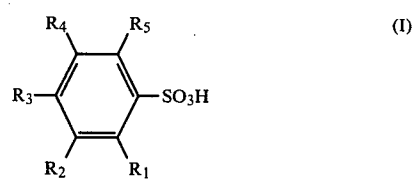

wherein $R_1$, $R_2$, $R_3$, $R_4$ and $R_5$ respectively, represent H, $SO_3H$, $NH_2$, COOH, OH, CN or $NO_2$ with dicyandiamide or melamine.

Suitable benzenesulfonic acid type compounds include benzenesulfonic acid, p-aminobenzenesulfonic acid, m-aminobenzenesulfonic acid, o-aminobenzenesulfonic acid, p-sulfobenzoic acid, m-sulfobenzoic acid, o-sulfobenzoic acid, p-phenolsulfonic acid, m-phenolsulfonic acid, o-phenolsulfonic acid, 2,4-phenoldisulfonic acid, 1,3,5-benzenetrisulfonic acid, p-benzenedisulfonic acid, m-benzenedisulfonic acid, p-nitrobenzenesulfonic acid and m-nitrobenzenesulfonic acid.

The benzenesulfonic acid type compounds should have at least one $SO_3H$ group and are not limited to said compounds.

These compounds have not satisfactory flame retardancy for polyamides, however, these compounds do not cause blooming.

On the other hand, dicyandiamide is used as a starting material for producing melamine, guanidine, guanamine and dicyandiamide resins.

Dicyandiamide has been produced in an industry with melamine.

When dicyandiamide or melamine is used as a flame retardant for polyamides, flame retardancy is given, but blooming is easily caused.

As described above, the benzenesulfonic acid type compound (I), dicyandiamide and melamine as flame retardants are not suitable as expected by the inventors.

The present invention is to obtain flame retardant having excellent characteristics by reacting two or more of these components.

The flame retardant of the present invention can be easily obtained by dissolving at least one of the benzenesulfonic acid type compound with dicyandiamide or melamine in a solvent and heating them. Thus, any reaction can be employed for reacting them as far as the reaction is enough.

A molar ratio of dicyandiamide and/or melamine to the benzenesulfonic acid type compound in the reaction system can be 0.5 to 3 and preferably, about 1.

Polyamides to which the flame retardant of the present invention is incorporated to give flame retardancy, include homopolyamides and copolyamides which are obtained by a polymerization of lactam or aminocapronic acid, or a copolymerization of diamine and dicarboxylic acid.

Typical polyamides include nylon 6, nylon 6,6, nylon 6,10, nylon 6,12, nylon 11, nylon 12 and copolymers thereof or mixtures thereof from the viewpoint of economical property and physical property. Polyamides can be also copolymers of nylon 6 or nylon 6,6 and a nylon salt wherein said nylon salt is obtained by reacting a dicarboxylic acid component such as terephthalic acid, isophthalic acid, adipic acid and sebacic acid with a diamine such as hexamethylenediamine, methaxylenediamine, para-aminocyclohexylmethane, and 1,4-bisaminomethylcyclohexane.

An amount of the flame retardant incorporated into the polyamide is usually in a range of from 3 to 30% by weight preferably from 5 to 20% by weight. When it is less than 3% by weight, the flame retardancy is inferior whereas when it is more than 30% by weight, the physical property of the polyamide is deteriorated or economical disadvantage is found.

The flame retardant of the present invention is effective at a smaller ratio in comparison with those of the conventional flame retardants. A specific gravity of the flame retardant polyamide composition with the flame retardant is lower than those of the conventional one. Therefore, the cost per unit volume is low to result remarkably advantageous effect.

When the flame retardant of the present invention is incorporated into the polyamide, a particle diameter is less than 100μ. It is necessary to pulverize it to particle diameters suitable for dispersing it into the polyamide, since when the particle diameter is too large, the flame retardant can not be miscible to the polyamide whereby the physical property is deteriorated and the appearance of a molded product is deteriorated.

In the present invention, a method of blending the flame retardant to the polyamide is not critical. It is enough to give a condition dispersing the flame retardant uniformly into the polyamide.

In particularly, the flame retardant is incorporated into the pellets of the polyamide and they are uniformly blended by a tumbler or Henschel mixer and kneaded by an extruder to pelletize the mixture and the pellets are molded.

In another method, pellets containing high content of the flame retardant (master batch) are prepared and blended with suitable polyamide pellets and the mixture is molded. In the other method, the flame retardant is dry-blended to pellets of the polyamide and the mixture is molded.

The flame retardant can be incorporated together with glass fiber; inorganic filler such as silica, talc, mica, magnesium hydroxide, aluminum hydroxide, calcium silicate, aluminum silicate and calcium carbonate; other flame retardant; heat-stabilizer; weathering-stabilizer; mold release agent; dispersing agent; lubricant; plasticizer; pigment, dye or foaming agent as desired.

The flame retardant polyamides which contain the flame retardant of the present invention, can be used for extrusion-molding, injection-molding, blow-molding and foaming.

The present invention will be further illustrated by certain examples and references which are provided for purposes of illustration only and are not intended to be limiting the present invention.

In the example, flameability, blooming and mechanical characteristics of test pieces were measured and evaluated by the following methods.

(1) Flameability:

Each test piece having a length of 5 inch, a width of ½ inch and a thickness of 1/32, 1/16 or ⅛ inch, was prepared and each flameability was measured by UL-94 (Standard of Under writer's Laboratories Inc.).

(2) Blooming:

Each disc having a thickness of ⅛ inch and a diameter of 100 mm was prepared and kept in an atmosphere of 90% RH at 40° C. for 1 week. The surface of the disc was observed.

(3) Mechanical characteristics:

In accordance with the Japanese Industrial Standard K 6810, each tensile strength was measured by using a #1 dumb'bell and each Izod impact strength was measured by using a square timber test piece having a length of 63.5 mm and a side of 12.7 mm.

EXAMPLE 1 and REFERENCE 1

Dicyandiamide and aniline-p-sulfonic acid at equivalent ratio were stirred in a hot water. The resulting reaction product (A) was filtered and dried and pulverized to give an average particle diameter of less than 50μ. The reaction product (A) was mixed with nylon 6 having a relative viscosity of 2.55 (measured by the method of Japanese Industrial Standard K6810) at a ratio of 20% by weight by a tumbler. The mixture was kneaded so as to uniformly disperse by an extruder having a diameter of 65 mm at 240° C., and pelletized and dried.

The pellets were used as a master and blended to nylon 6 so as to form the compositions shown in Table 1. Each mixture was molded by an injection-molding machine at 230° C. of a cylindrical temperature to prepare each test piece.

As a reference, each test piece was also prepared without incorporating any flame retardant or with 10% by weight of cyanuric acid or melamine instead of the flame retardant.

Tests were carried out by using these test pieces. The results are shown in Table 1.

TABLE 1

| Example and Reference | Exp. 1 | | | | Ref. 1 | | |
| --- | --- | --- | --- | --- | --- | --- | --- |
| Test No. | 1 | 2 | 3 | 4 | 1 | 2 | 3 |
| Reaction Product (A) (wt. %) | 20 | 15 | 10 | 5 | — | — | — |
| Cyanuric acid (wt. %) | — | — | — | — | — | 10 | — |
| Melamine (wt. %) | — | — | — | — | — | — | 10 |
| Flameability (UL-94) | | | | | | | |
| ⅛" | V-0 | V-0 | V-0 | V-0 | V-2 | V-0 | V-0 |
| 1/16" | V-0 | V-0 | V-0 | V-0 | V-2 | V-0 | V-0 |
| 1/32" | V-0 | V-0 | V-0 | V-0 | V-2 | V-0 | V-0 |
| Blooming | none | none | none | none | none | blooming | blooming |
| Tensile strength (kg/cm$^2$) | 741 | 748 | 766 | 793 | 816 | 745 | 683 |
| Izod impact strength (kg . cm/cm | 2.9 | 3.3 | 4.1 | 5.2 | 6.4 | 2.8 | 3.2 |

TABLE 1-continued

| Example and Reference | Exp. 1 | | | | Ref. 1 | | |
|---|---|---|---|---|---|---|---|
| Test No. | 1 | 2 | 3 | 4 | 1 | 2 | 3 |
| notch) | | | | | | | |

EXAMPLE 2

In accordance with the process of Example 1, 10% by weight of the reaction product (A) was incorporated into each homopolymer of nylon 6, nylon 6,6 or nylon 12 or each copolymer of nylon 6/6,6(molar ratio of 93:7; melting point of 196° C.), nylon 6/6 MXD (molar ratio of 93:7; melting point of 189° C.; MXD is a salt of adipic acid with metaxylenediamine) and each mixture was pelletized at a temperature of about 20° C. above the melting point and molded to prepare each test piece and the tests were carried out. The results are shown in Table 2.

TABLE 2

| Example 2 Test No. | 1 | 2 | 3 | 4 | 5 |
|---|---|---|---|---|---|
| Resin | Nylon 6 | Nylon 6,6 | Nylon 12 | Nylon 6/6,6 | Nylon 6/6 MXD |
| Reaction product (A) (wt. %) | 10 | 10 | 10 | 10 | 10 |
| Flameability (UL-94) | | | | | |
| 1/8" | V-0 | V-0 | V-0 | V-0 | V-0 |
| 1/16" | V-0 | V-0 | V-0 | V-0 | V-0 |
| 1/32" | V-0 | V-0 | V-0 | V-0 | V-0 |
| Blooming | none | none | none | none | none |

EXAMPLE 3

Melamine and aniline-p-sulfonic acid at equivalent ratio were stirred in a hot water and treated by the process of Example 1 to obtain a reaction product (B) in a fine powdery form.

In accordance with the process of Example 1 except using 10% by weight of the reaction mixture (B), each composition was prepared and tests were carried out. The results are shown in Table 3 together with those of References.

TABLE 3

| Example and Reference | Exp. 3 | | | | Ref. 1 | | |
|---|---|---|---|---|---|---|---|
| Test No. | 1 | 2 | 3 | 4 | 1 | 2 | 3 |
| Reaction product (B) (wt. %) | 20 | 15 | 10 | 5 | — | — | — |
| Cyanuric acid (wt. %) | — | — | — | — | — | 10 | — |
| Melamine (wt. %) | — | — | — | — | — | — | 10 |
| Flameability (UL-94) | | | | | | | |
| 1/8" | V-0 | V-0 | V-0 | V-0 | V-2 | V-0 | V-0 |
| 1/16" | V-0 | V-0 | V-0 | V-0 | V-2 | V-0 | V-0 |
| 1/32" | V-0 | V-0 | V-0 | V-0 | V-2 | V-0 | V-0 |
| Blooming | none | none | none | none | none | blooming | blooming |
| Tensile strength (Kg/cm²) | 752 | 767 | 775 | 803 | 816 | 745 | 683 |
| Izod impact strength (kg · cm/cm notch) | 2.7 | 3.5 | 4.3 | 5.1 | 6.4 | 2.8 | 3.2 |

TABLE 3-continued

| Example and Reference | Exp. 3 | | | | Ref. 1 | | |
|---|---|---|---|---|---|---|---|
| Test No. | 1 | 2 | 3 | 4 | 1 | 2 | 3 |
| notch) | | | | | | | |

EXAMPLE 4

In accordance with the process of Example 1, 10% by weight of the reaction product (B) obtained in Example 3 was incorporated into each homopolymer of nylon 6 or nylon 12 or a copolymer of nylon 6/6,6 (molar ratio of 93:7; melting point of 196° C.) and each mixture was pelletized at a temperature of about 20° C. above the melting point and molded to prepare each test piece and the tests were carried out. The results are shown in Table 4.

TABLE 4

| Example 4 Test No. | 1 | 2 | 3 |
|---|---|---|---|
| Resin | Nylon 6 | Nylon 12 | Nylon 6/6,6 |
| Reaction product (B) (wt. %) | 10 | 10 | 10 |
| Flameability (UL-94) | | | |
| 1/8" | V-0 | V-0 | V-0 |
| 1/16" | V-0 | V-0 | V-0 |
| 1/32" | V-0 | V-0 | V-0 |
| Blooming | none | none | none |

EXAMPLE 5

In accordance with the process of Example 1, 10% by weight of a reaction product (C) obtained by reacting dicyandiamide with p-phenolsulfonic acid and 0.1% by weight of magnesium stearate were incorporated into nylon 6 by a Henschel mixer and a test piece was prepared and tested. As the result, flameabilities at 1/8", 1/16" and 1/32" were respectively V-0 and blooming was not caused. The results are shown in Table 5.

EXAMPLE 6

In accordance with the process of Example 1, 10% by weight of a reaction product (D) obtained by reacting dicyandiamide with benzenesulfonic acid was incorporated into nylon 6 and a test piece was prepared and tested.

The resulting composition had satisfactorily low flameability and no blooming. The results are shown in Table 5.

EXAMPLE 7

In accordance with the process of Example 1, 10% by weight of the reaction product (A) and 0.1% by weight of cuprous chloride were incorporated and a test piece was prepared and tested.

The resulting composition had satisfactorily low flameability and no blooming. The results are shown in Table 5.

EXAMPLE 8

In accordance with the process of Example 1, 10% by weight of a reaction product (E) obtained by reacting melamine with aniline-m-sulfonic acid and 0.1% by weight of lithium stearate were incorporated into nylon 6 by a blender and a test piece was prepared and tested.

The resulting composition had satisfactorily low flameability and no blooming. The results are shown in Table 5.

EXAMPLE 9

In accordance with the process of Example 1, 15% by weight of a reaction product (F) obtained by reacting melamine with p-phenol-sulfonic acid (molar ratio of 1:1), 0.1% by weight of manganese phosphate and 0.05% by weight of calcium stearate were incorporated in nylon 6 and a test piece was prepared and tested. The resulting composition had satisfactorily low flameability and no blooming. The results are shown in Table 5.

EXAMPLE 10

In accordance with the process of Example 1, 5% by weight of a reaction product (G) obtained by reacting melamine with p-benzenedisulfonic acid (molar ratio of 1:1) and 5% by weight of the reaction product (A) were incorporated into nylon 6/6,6 (molar ratio of 93:7; melting point of 196° C.) and a test piece was prepared and tested.

The resulting composition had satisfactorily low flameability and no blooming. The results are shown in Table 5.

TABLE 5

| Example | 5 | 6 | 7 | 8 | 9 | 10 |
|---|---|---|---|---|---|---|
| Resin | Nylon 6 | Nylon 6 | Nylon 6 | Nylon 6 | Nylon 6 | Nylon 6/6,6 |
| Flame retardant | (C) | (D) | (A) | (E) | (F) | (A) + (G) |
| Reaction product (wt. %) | 10% | 15% | 10% | 10% | 15% | 5% 5% |
| Additives (wt. %) | S . Mg 0.1% | — | CuCl 0.1% | S . Li 0.1% | P . Mn 0.1% S . Ca 0.05% | — |
| Flameability (UL-94) | | | | | | |
| 1/8" | V-0 | V-0 | V-0 | V-0 | V-0 | V-0 |
| 1/16" | V-0 | V-0 | V-0 | V-0 | V-0 | V-0 |
| 1/32" | V-0 | V-0 | V-0 | V-0 | V-0 | V-0 |
| Blooming | none | none | none | none | none | none |
| Tensile strength (kg/cm$^2$) | 794 | 757 | 763 | 772 | 776 | 785 |
| Izod impact strength (kg . cm/ cm . notch) | 4.8 | 3.9 | 4.0 | 4.5 | 3.7 | 4.1 |

What is claimed is:

1. A flame retardant for a polyamide which is a reaction product obtained by reacting a benzenesulfonic acid compound having the formula:

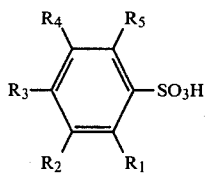

wherein $R_1$, $R_2$, $R_3$, $R_4$ and $R_5$ each represents H, SO$_3$H, NH$_2$, COOH, OH, CN or NO$_2$, with dicyandiamide, the molar ratio of said dicyandiamide to said benzenesulfonic acid compound ranging from 0.5 to 3.

2. The flame retardant for a polyamide according to claim 1, wherein said reaction product is obtained by reacting benzenesulfonic acid with dicyandiamide.

3. The flame retardant for a polyamide according to claim 1, wherein said reaction product is obtained by reacting sulfanilic acid with dicyandiamide.

4. The flame retardant for a polyamide according to claim 1, wherein said reaction product is obtained by reacting p-phenolsulfonic acid with dicyandiamide.

5. A flame retardant composition, which comprises: a polyamide and a flame retardant amount of a flame retardant reaction product obtained by reacting a compound having the formula:

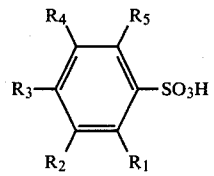

wherein $R_1$ to $R_5$ each represents H, SO$_3$H, NH$_2$, COOH, OH, CN, or NO$_2$, with dicyandiamide, the molar ratio of said dicyandiamide to said benzenesulfonic acid compound ranging from 0.5 to 3.

6. The flame retardant polyamide composition according to claim 5 wherein said flame retardant is incorporated in said composition at a ratio of from 3 to 30 wt.%.

7. The flame retardant polyamide composition according to claim 6 wherein said polyamide is polycaprolactam.

8. The flame retardant polyamide composition according to claim 6 wherein said polyamide is polyhexamethyleneadipamide.

9. The flame retardant polyamide composition according to claim 6 wherein said polyamide is polycaprolactam containing at least one additive selected from the group consisting of glass fibers, heat stabilizers, weathering stabilizers, mold release agents, dispersing agents, lubricants, plasticizers, pigments, dyes and foaming agents.

10. The flame retardant polyamide composition according to claim 6 wherein said polyamide is polyhexamethyleneadipamide containing at least one additive selected from the group consisting of glass fibers, heat stabilizers, weathering stabilizers, mold release agents, dispersing agents, lubricants, plasticizers, pigments, dyes and foaming agents.

11. The flame retardant polyamide composition according to claim 5, wherein said flame retardant of claim 3 is incorporated in said composition at a ratio of from 3 to 30 weight percent.

12. The flame retardant polyamide composition according to claim 5, wherein said flame retardant of claim 4 is incorporated in said composition at a ratio of from 3 to 30 wt.%.

13. The flame retardant polyamide composition according to claim 11, wherein said polyamide is polycaprolactam.

14. The flame retardant polyamide composition according to claim 12, wherein said polyamide is polycaprolactam.

15. The flame retardant polyamide composition according to claim 11, wherein said polyamide is a copolyamide or contains a copolyamide.

16. The flame retardant polyamide composition according to claim 12, wherein said polyamide is a copolyamide or contains a copolyamide.

* * * * *